United States Patent [19]

Ueno et al.

[11] Patent Number: 4,840,941
[45] Date of Patent: Jun. 20, 1989

[54] METHOD FOR INHIBITING INFECTION OF HUMAN T-CELLS

[75] Inventors: Ryuzo Ueno, Nishinomiya; Ryuji Ueno, Kyoto; Sachiko Kuno, Ibaraki; Akihiko Tabata, Nishinomiya, all of Japan

[73] Assignee: Kabushiki Kaisha Ueno Seiyaku Oyo Kenkyujo, Japan

[21] Appl. No.: 144,131

[22] Filed: Jan. 15, 1988

Related U.S. Application Data

[62] Division of Ser. No. 19,180, Feb. 26, 1987.

[30] Foreign Application Priority Data

| Apr. 4, 1986 [JP] | Japan | 61-078470 |
| Apr. 4, 1986 [JP] | Japan | 61-078471 |
| Apr. 21, 1986 [JP] | Japan | 61-093019 |

[51] Int. Cl.$^4$ ............ A61K 31/70; A61K 31/72; A61K 31/725; C08B 37/02
[52] U.S. Cl. .................. 514/59; 514/55; 514/56; 514/60; 514/54; 536/20; 536/21; 536/51; 536/54; 536/58
[58] Field of Search ............ 514/55, 56, 54, 59, 514/60; 536/20, 21, 51, 54, 58

[56] References Cited

U.S. PATENT DOCUMENTS

| 4,374,832 | 2/1983 | Joseph et al. | 514/25 |
| 4,522,814 | 6/1985 | Nonomura et al. | 514/54 |
| 4,590,181 | 5/1986 | McCarthy | 536/112 |
| 4,710,493 | 12/1987 | Landsberger | 514/56 |
| 4,734,403 | 3/1988 | Dussourd D'Ainterland | 514/54 |

FOREIGN PATENT DOCUMENTS

| 0012625 | 9/1983 | Australia. | |
| 0012631 | 9/1983 | Australia. | |
| 1146859 | 5/1983 | Canada | 167/177 |
| 0066379 | 12/1982 | European Pat. Off. | 514/59 |
| 3601136 | 7/1987 | Fed. Rep. of Germany. | |

OTHER PUBLICATIONS

Solomon et al; J. Bacteriology, 92(6):1855–1856 (1966).
Kiehl et al; J. Nat. Cancer Inst. 51(5):1705–1707 (1973).
S. Chaffrath et al; Hoppe-Seyler's Z. Physiol. Chem. 357:499–498 (1976).
Ito et al; Antiviral Research, 7:361–367 (1987).
Hirose et al; Biochem. Biophys. Res. Commun. 149(2): 662–667 (1987).
Tochikura et al; Jpn. J. Cancer Res., 78:583–589 (1987).
Nakashima et al; Antimicrob. Agents Chemother., 31(10):1524–1528 (1987).
Sydow et al; Biomed. Biochem. ACTA, 46(6), 527–530 (1987).
Nagumo et al; Jpn. J. Cancer Res., 79:9–11 (1988).
Nakashima et al; Jpn. J. Cancer Res., 78:1164–1168 (1987).
DiCioccio et al, Cancer Research, 38, 2401–2407 (1978).
Ehlers et al, J. Gen Virol (1984), 65, 423–428 and 1325–1330.
Walton, British Journal Pharmacology, 7, 370 (1952), 8, 340 (1953) and 9, 1 (1954).
Ricketts, Biochem., 51, 129 (1952).

*Primary Examiner*—Ronald W. Griffin
*Assistant Examiner*—Nancy S. Carson
*Attorney, Agent, or Firm*—Sughrue, Mion, Zinn, Macpeak and Seas

[57] ABSTRACT

Method of treatment of diseases caused by retroviruses which comprises administering therapeutically effective amount of a natural or synthetic oligo- or polysaccharide having at least one S-oxoacid group attached to the saccharic carbon atom through a linking group of lower molecular weight or a pharmaceutically acceptable salt thereof to a subject in need of such treatment.

11 Claims, 14 Drawing Sheets

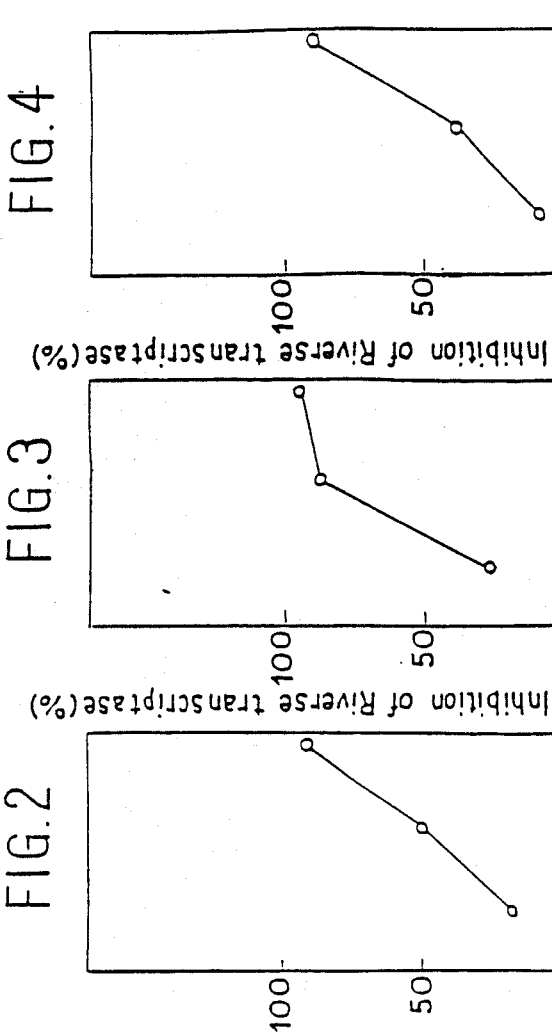

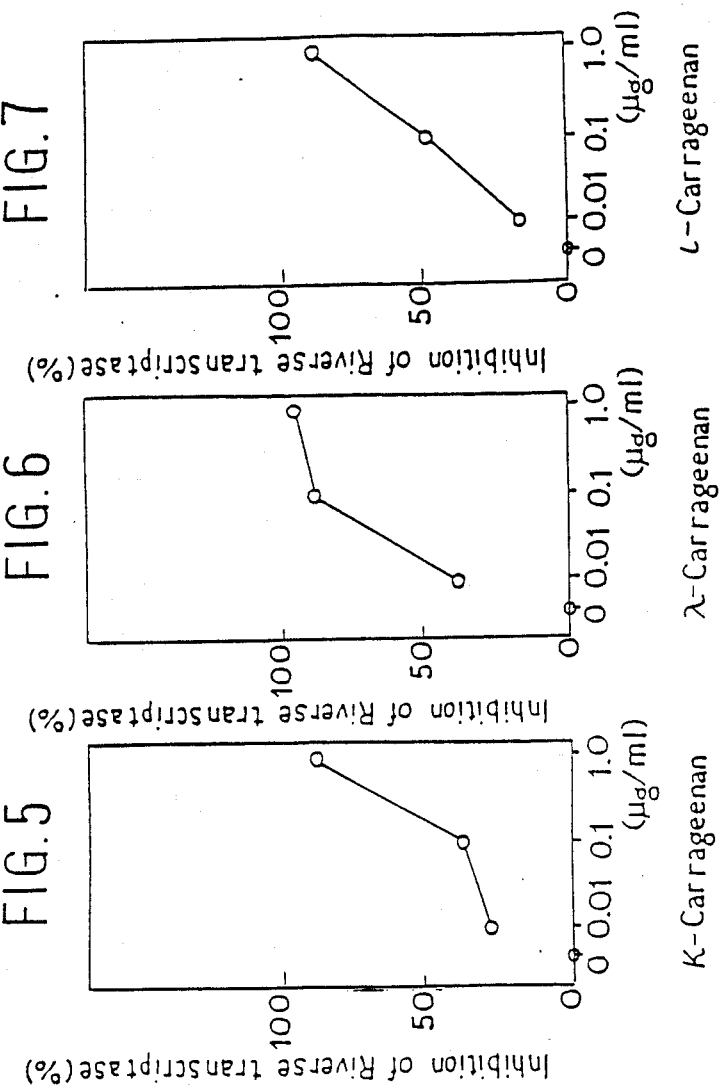

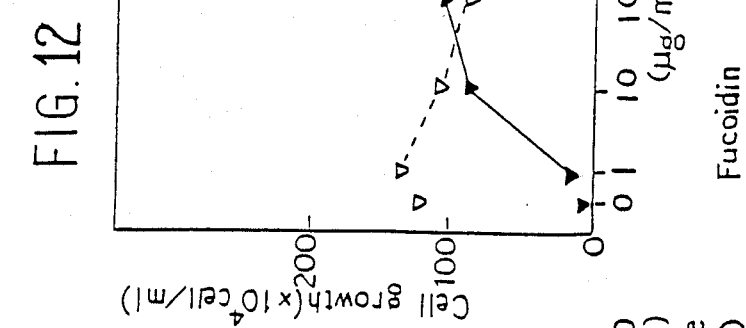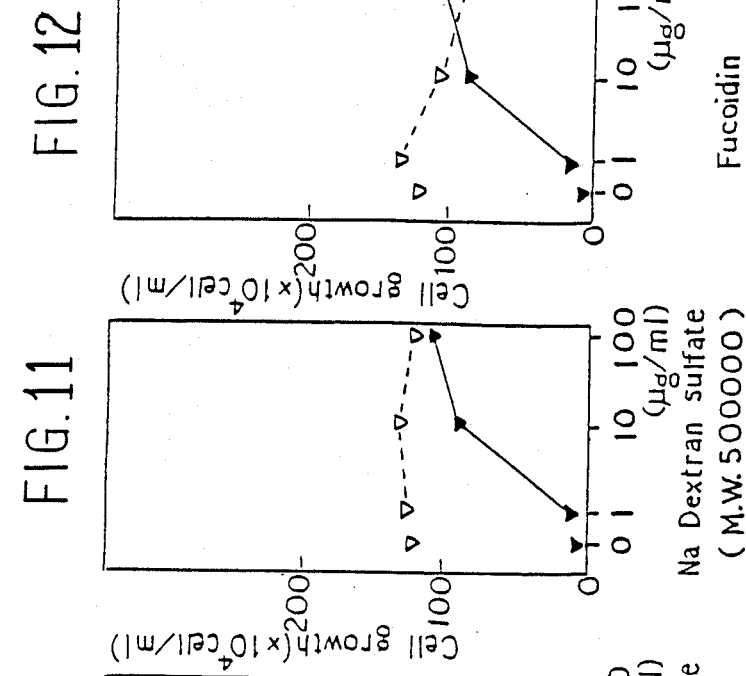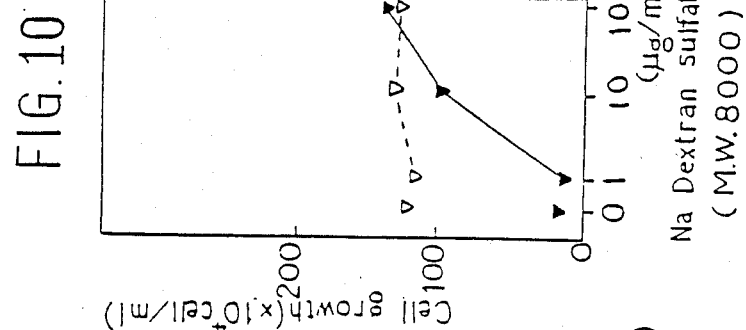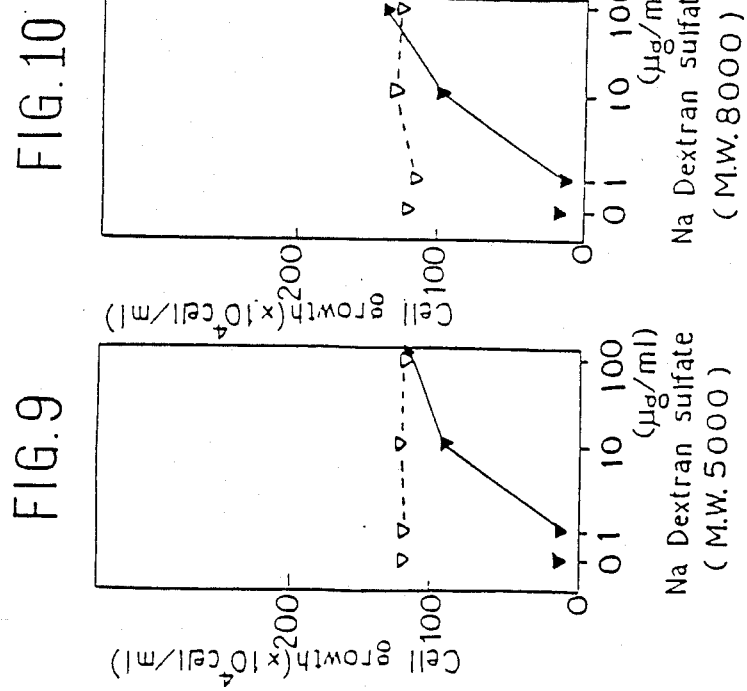

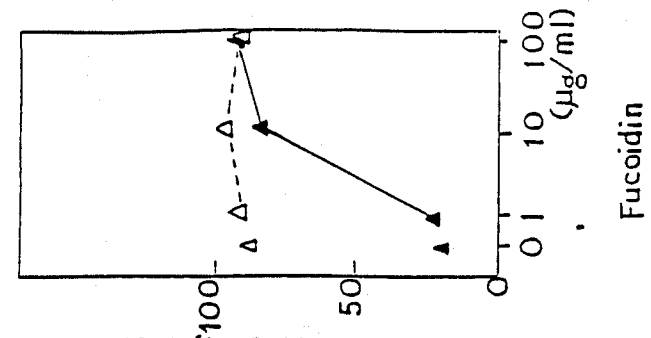
FIG. 19
FIG. 18
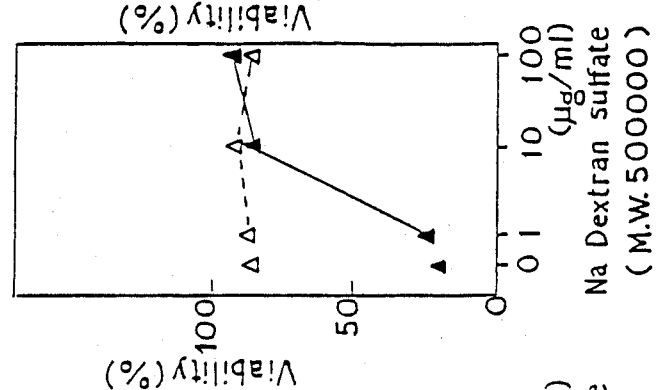
FIG. 17
FIG. 16
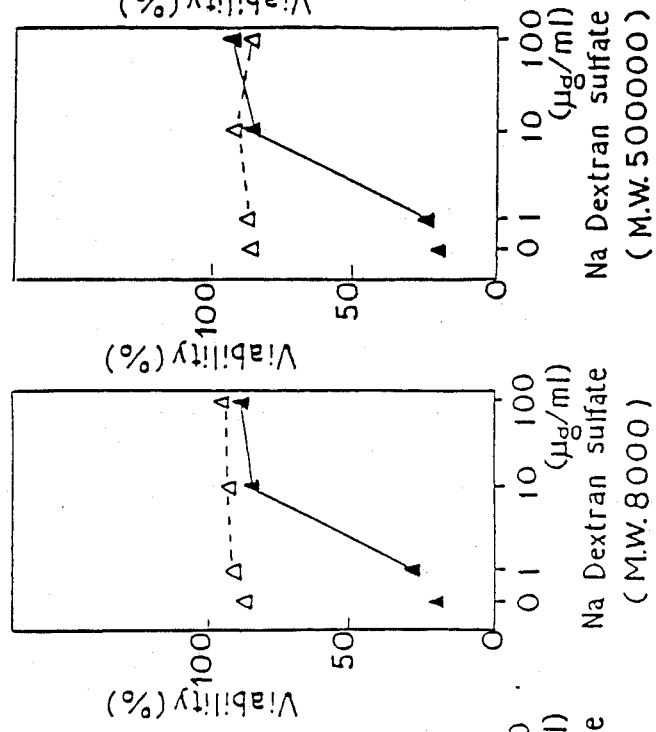
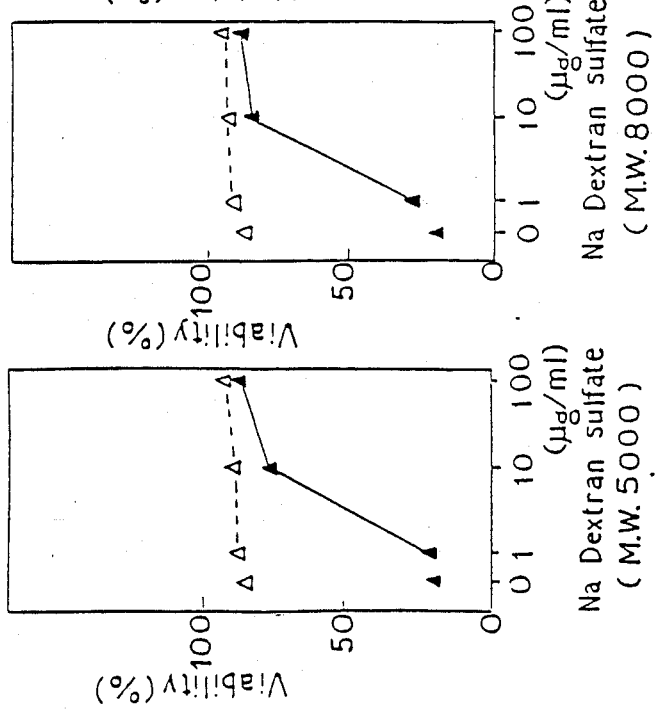

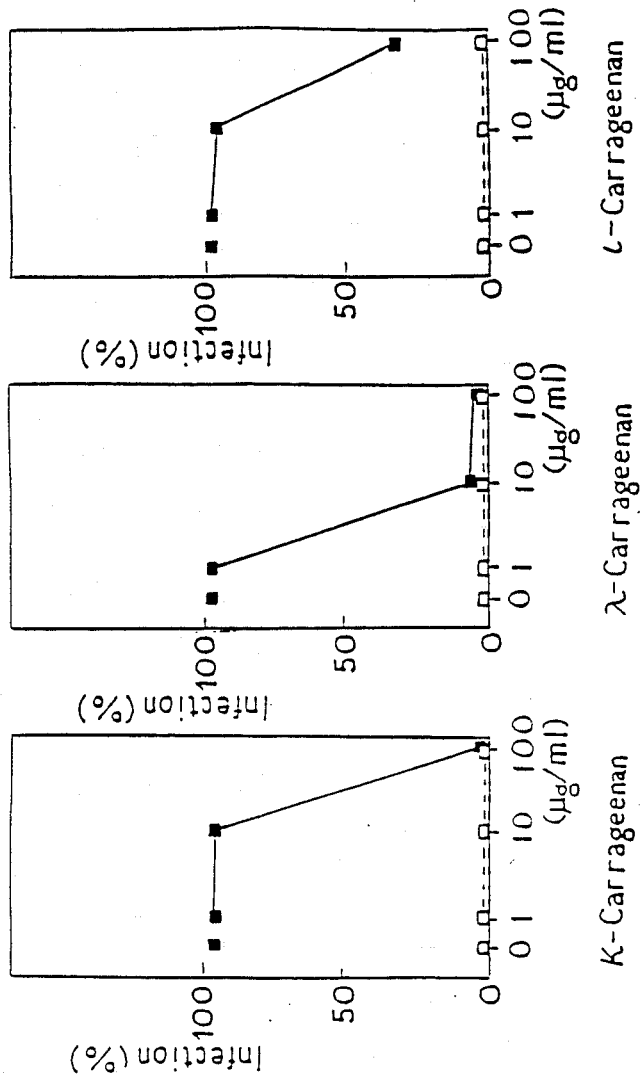

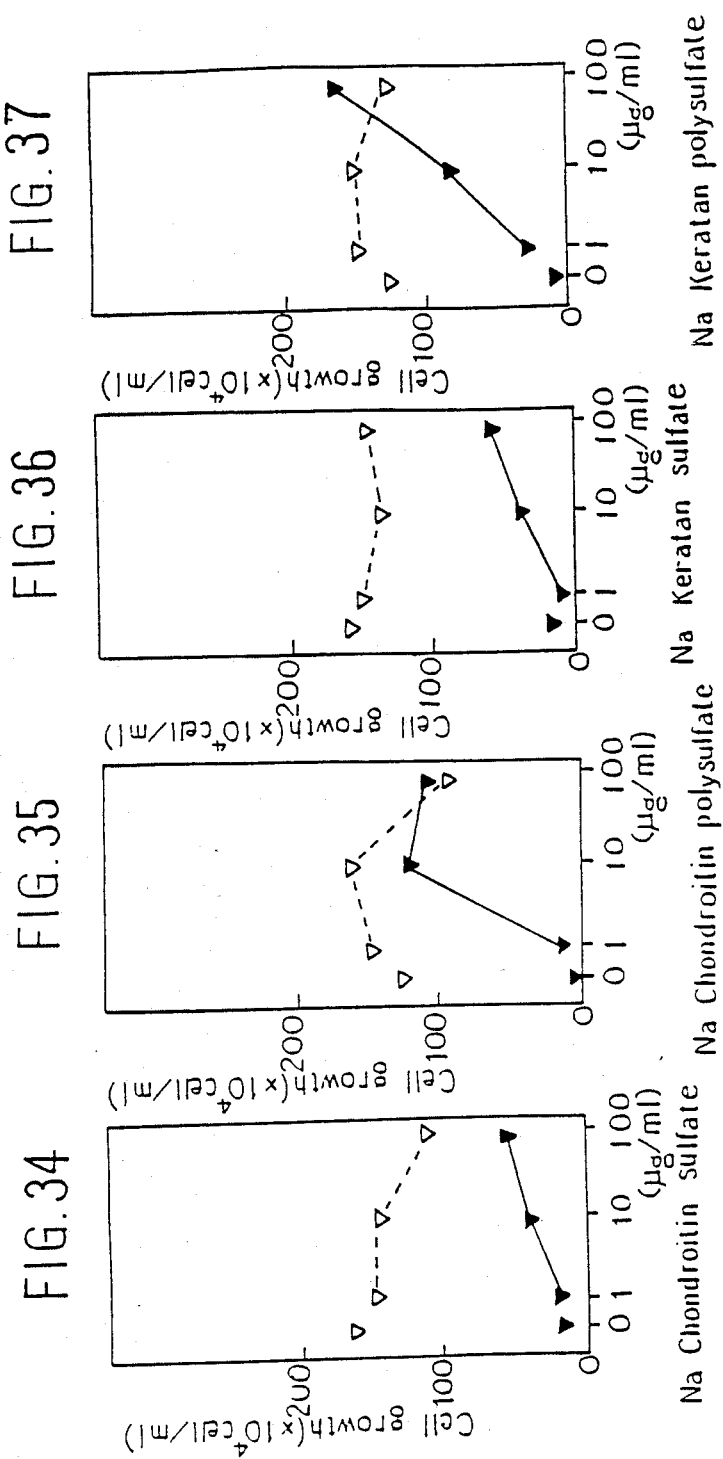

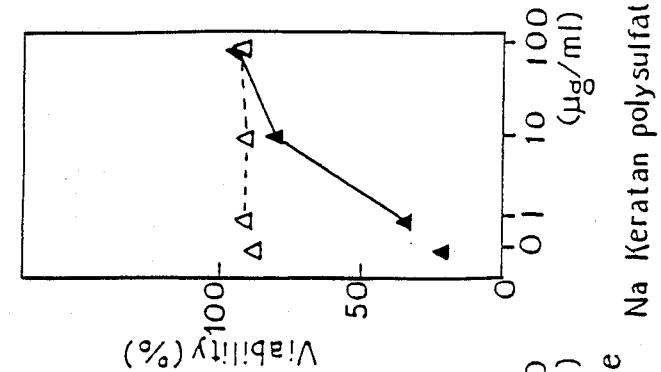
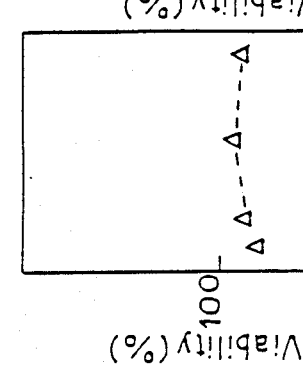
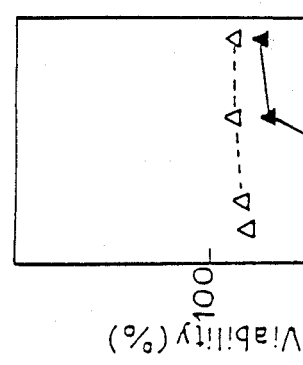
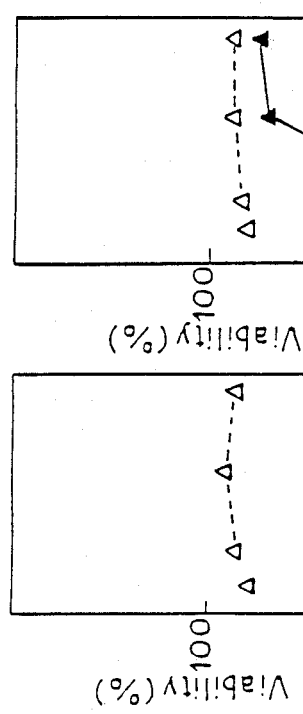

METHOD FOR INHIBITING INFECTION OF HUMAN T-CELLS

This is a division of application Ser. No. 019,180 filed 2/26/87.

FIELD OF THE INVENTION

The present invention relates to prevention, therapy, etc. of diseases caused by retroviruses. More particularly, the present invention provides a medicament (including veterinary medicament) containing as active ingredient a natural or synthetic oligo- or polysaccharide having at least one S-oxoacid group attached to the saccharic carbon atom through a linking group of lower molecular weight or a pharmaceutically acceptable salt thereof and a method of prevention and therapy etc. of the diseases caused by retroviruses, especially AIDS (acquired immune deficiency syndrome), ARC(AIDS-related complex), PGL (persistent generalized lymphadenopathy) and AIDS-virus carrier using such medicament.

BACKGROUND OF THE INVENTION

The term "Retroviruses" refer to a family of viruses which contain RNA and which encode a reverse transcriptase (RNA-dependent DNA polymerase). The reverse transcriptase, which is capable of using the viral RNA as a template for the synthesis of complementary DNA, is essential to the first stage of the virus' self-replication.

Retroviruses include various oncoviruses such as avian leukemia virus, avian sarcoma virus, avian reticuloendotheliosis virus, murine mammary cancer virus, murine leukemia virus, murine sarcoma virus, guinea pig type C virus, hamster type C virus, rat leukemia virus, feline leukemia virus, feline sarcoma virus, feline type C virus, ovine leukemia virus, bovine leukemia virus, swine type C virus, simian leukemia virus, Mason-Pfizer virus, simian sarcoma virus, simian T-lymphotropic virus, baboon type C virus, and the like. Among those infective to human, important ones are adult T-cell leukemia virus (ATLV), or human T-lymphotropic virus type I (HTLV-I), and type II (HTLV-II). The adult T-cell leukemia abounds in Japan, especially in the west part, but the effective treatment containing prevention and therapeutics of the disease has not been established.

On the other hand, retroviruses also include those having no oncogenecity, such as visna virus, ovine progressive pneumonia virus, ovine maedi virus, simian T-lymphotropic virus type III (STLV-III), equine infectious anemia virus, and the like. The viruses isolated from human as causative agents for AIDS or ARC etc. (HTLV-III, LAV1, LAV2, ARV, and other so-called AIDS-viruses.) belong to this subfamily. Recently, AIDS-causative viruses have been termed HIVs (human immune deficiency viruses).

A third subfamily includes viruses such as a spumavirinae to which the simian foaming virus belongs. In addition, a retrovirus has recently been isolated as a causative virus for Kawasaki disease (mucocutaneous lymphonode syndrome).

World-wide interests have been focused on AIDS due to its unfavorable prognosis. It is a clinical syndrome characterized by recurrent oppotunistic infections, (e.g. pneumocystis carinii pneumonia, cryptococcal meningitis, disseminated toxoplasmosis), lymphadenopathy, and an aggressive Kaposi's sarcoma, and induces a high mortality more than 90% by the dysregulation of immune system. It is also known that the helper-T cells are specifically destroyed by the infection of the virus.

In order to find out pharmaceutical agents effective on the treatment of AIDS, ARC, PGL, and AIDS-virus carrier, the present inventors, using a cell line of MT-4 established from T-cells of adult T-cell leukemia patient and HTLV-III which is a causative virus for AIDS, examined the effects of various substances on the infection and replication of HTLV-III.

The above MT-4 cell line is absolutely susceptible to infection with HTLV-III. Infection followed by cell lysis (experimental HTLV-III infection). The present inventors have found that when certain polysaccharides having sulfonate group ($-SO_3-$) or mucopolysaccharides having sulfonate group or their additionally sulfuric acid esterified derivatives were added to the experimental HTLV-III infection system, the infection of HTLV-III on MT-4 cells and viral replication were strongly inhibited without any accompanying toxicity to the cells.

Further, the present inventors demonstrated that the above polymerized sugar inhibits the reverse transcriptase of the retrovirus in vitro, and thereby suppresses the replication of the virus.

RELATED DISCLOSURES

Among the sulfuric acid esters of polysaccharides, dextran sulfate with lower molecular weight has long been commercialized as an antilipemic or anti-arteriosclerosis agent. Also, dextran sulfate with relatively higher molecular weight is known to have an inhibitory action against herpes virus. (European Patent Laid-Open Publication No. 0066379). However, since the herpes virus is a DNA virus, its replication fundamentally differs from that of the retrovirus which depends entirely on reverse transcriptase for synthesis of DNA. Accordingly, the effectiveness of dextran sulfate against herpes virus does not necessarily mean that it will have any effectiveness against retroviruses. Moreover, dextran sulfate wtih lower molecular weight less than 10,000 was found to be almost ineffective on herpes viruses.

Among the mucopolysaccharides or these sulfates, chondroitin sulfate is commercialized as a drug for sensorineural hearing impairment, neuralgia, lumbago and chronic nephritis, and also as a cornea-protective ophthalmic solution. Keratan sulfate is obtainable from the cartilage, teichuronic acid from the cell walls of *Bacillus subtilis,* hyaluronic acid from shark skin, whale cartilage, or from human serum, heparan sulfate from bovine liver or lung, and chitin from arthropod or from fungus or yeast, respectively. The process for preparing the further sulfuric acid esterified compound of chondroitin sulfate is described in Japanese Patent Publication (JP, B2) No. 9570/1971.

Heparin is known to inhibit various enzymes in vitro, e.g., DNA polymerase of phytohemagglutinin stimulated human lymphocytes and reverse transcriptase of simian sarcoma virus (Cancer Research, 38, 2401–2407), but is not proved to inhibit the viral infection of cells.

SUMMARY OF THE INVENTION

In one aspect, the present invention provides a method of treatment of diseases caused by retroviruses which comprises administering an effective amount of a natural or synthetic oligo- or polysaccharide having at least one S-oxoacid group attached to the saccharic carbon atom through a linking group of lower molecular weight or a pharmaceutically acceptable salt thereof to a subject in need of such treatment.

In another aspect, the present invention provides a use of the above oligo- or polysaccharide or a salt thereof for the manufacture of a medicament for treatment of diseases caused by retroviruses.

In a further aspect, the present invention provides a pharmaceutical composition comprising the above oligo- or polysaccharide or a salt thereof as an active ingredient in association with a pharmaceutically acceptable carrier, diluent or excipient.

BRIEF EXPLANATION OF THE DRAWINGS

FIGS. 1-7 show the reverse transcriptase inhibition activities of the test substances in Example 1.

FIGS. 9-15, 16-22, and 23-29 show the effects of the test substances on cell growth, viability, and infected cell rate (%) of MT-4 cells infected with HTLV-III, respectively, in Example 3.

FIGS. 34-37, 38-41, 42-45 show the effects of the test substances on cell growth, viability, and infected cell rate (%) of MT-4 cells infected with HTLV-III, repectively, in Example 6.

DETAILED DESCRIPTION AND PREFERRED EMBODIMENT

Figure 8:
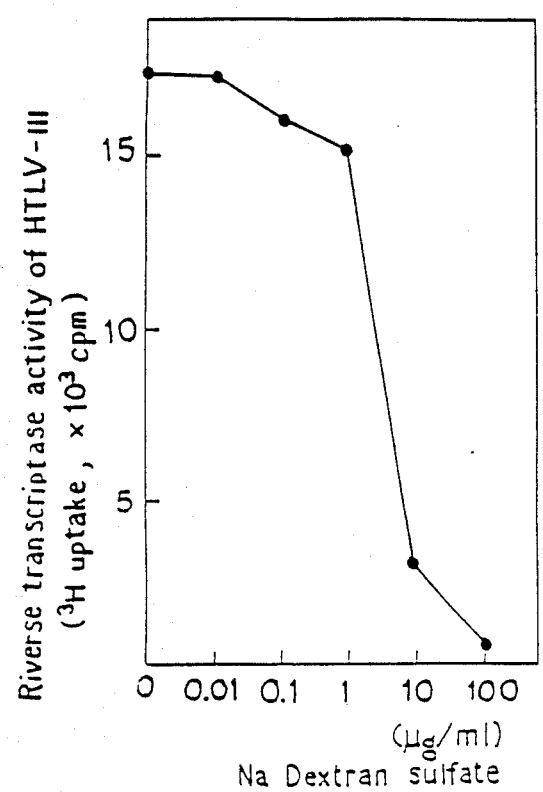
FIG. 8 shows the reverse transcriptase inhibition activity of the test substance in Example 2.
Figure 13:
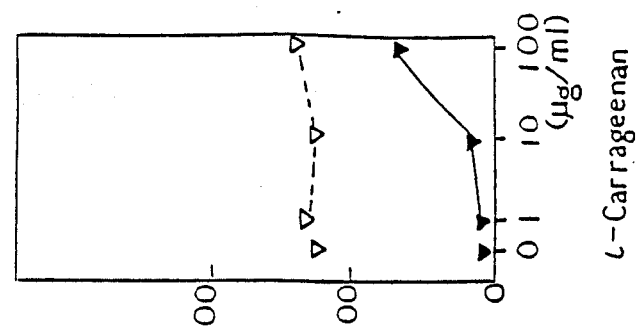
Figure 14:
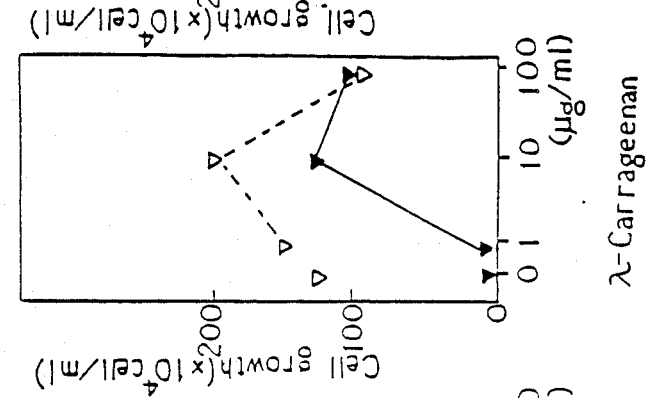
Figure 15:
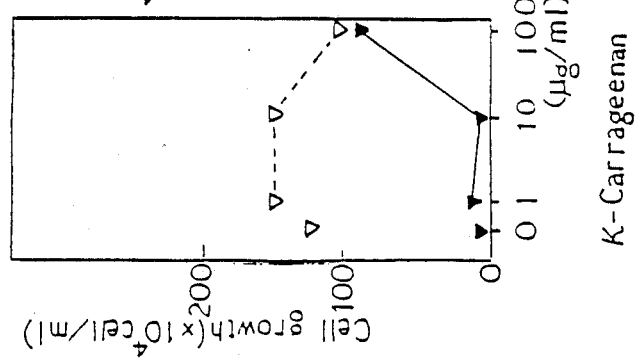
Figure 22:
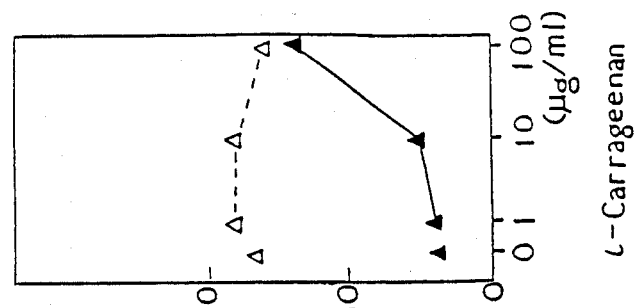
Figure 21:
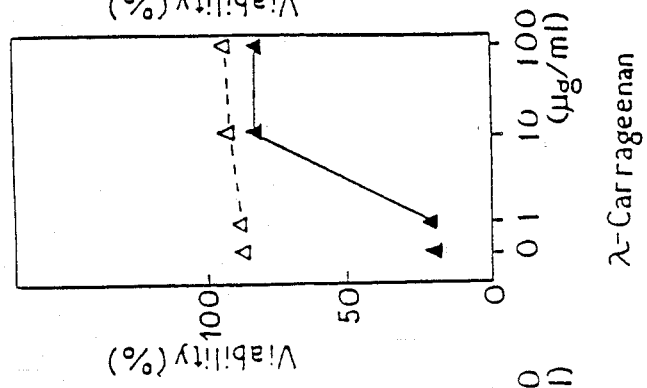
Figure 20:
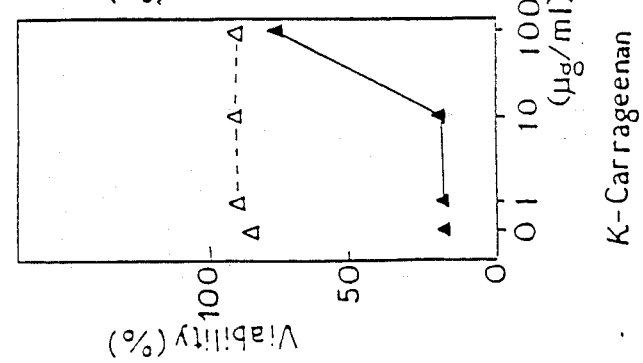
Figure 26:
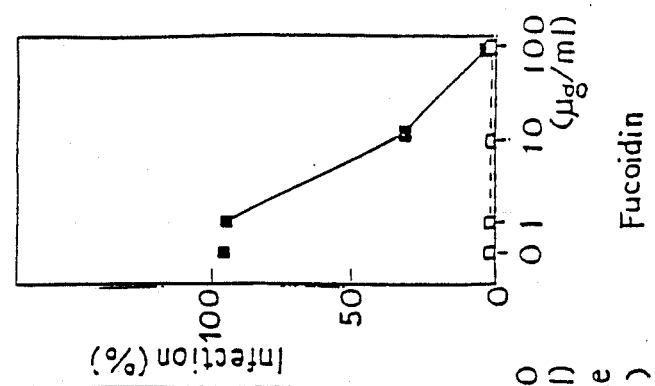
Figure 25:
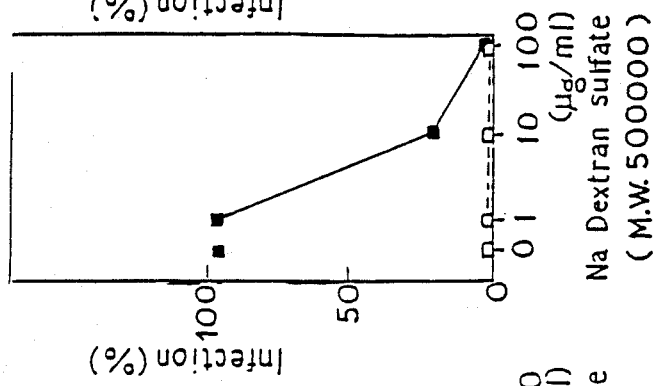
Figure 24:
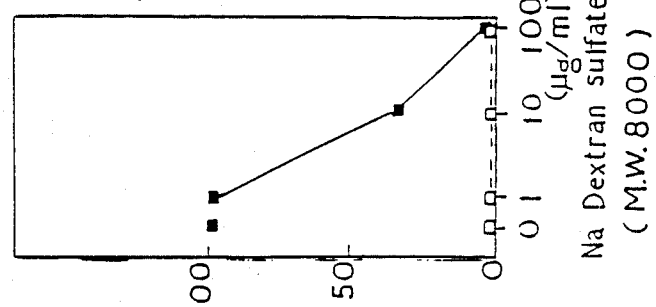
Figure 23:
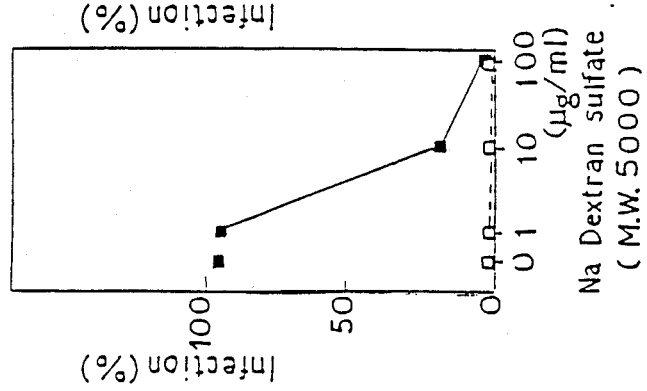
Figure 30:
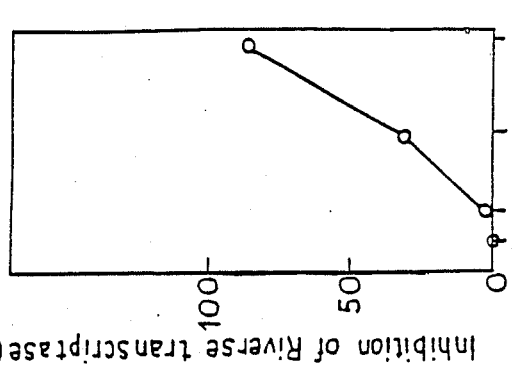
FIGS. 30-33 show the reverse transcriptase inhibition activities of the test substance in Example 5.
Figure 31:
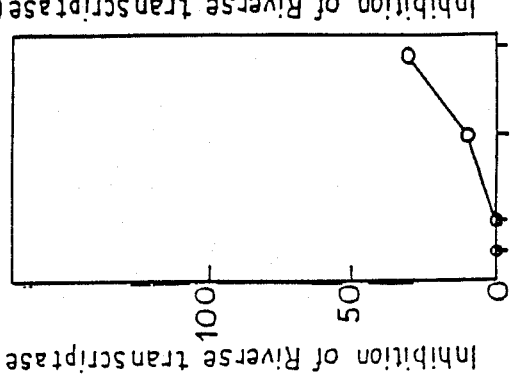
Figure 32:
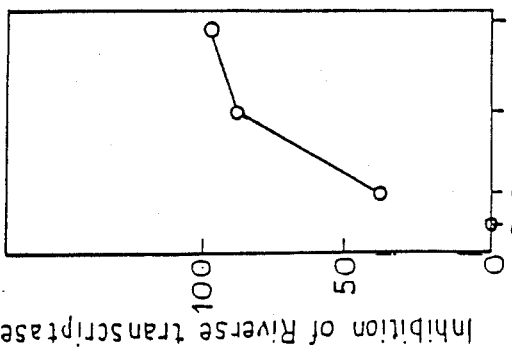
Figure 33:
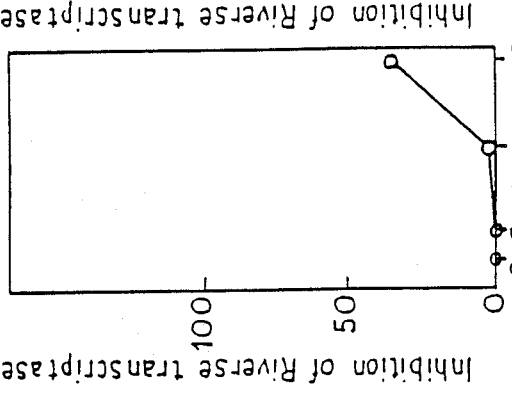
Figure 45:
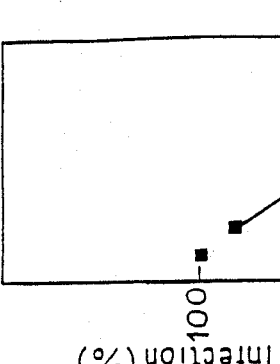
Figure 44:
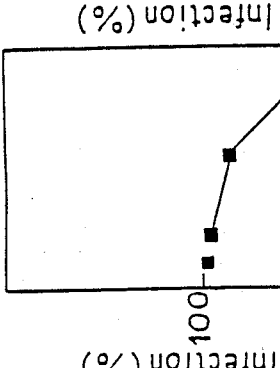
Figure 43:
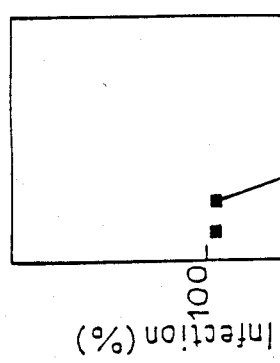
Figure 42:
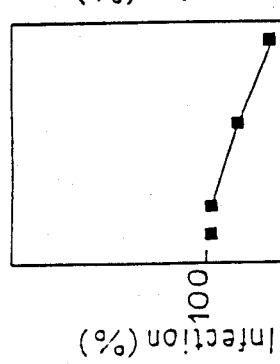

The term "treatment" herein is intended to cover all controls of disease including prevention, sustension (i.e. prevention of aggravation), reducing (i.e. alleviation of conditions) and therapy.

The term "retroviruses" includes all viruses having RNA and reverse transcriptase as their basic components. Examples of retroviruses are provided above.

The diseases referred to herein cover all the diseases caused by retroviruses, including those bearing or not bearing the aforementioned virus name. Important diseases are the diseases caused by AIDS-viruses.

The oligo- or polysaccharide usable in the present invention are those having at least one S-oxoacid group attached to the saccharic carbon atom through a linking group of lower molecular weight. Such oligo- or polysaccharide may be natural or synthetic. The term "natural" is intended to mean that the oligo- or polysaccharide is obtainable from a natural source such as plant, microorganism or animal by extraction and other means. The term "synthetic" is intended to mean that the oligo- or polysaccharide is obtainable synthetically, for example, by introducing S-oxoacid group into other oligo- or polysaccharide which has or has not S-oxoacid group and which is natural or unnatural (and synthetic).

The term "oligosaccharide" refers to a carbohydrate containing from two up to about nine monosaccharides linked together. For example, when an oligosaccharide contains three monosaccharides, one, two or three of the monosaccharides may have at least one S-oxoacid group.

The term "polysaccharide" refers to a carbohydrate containing about ten or more monosaccharides linked together. At least one and possibly most or all of the monosaccharides may have at least one and normally up to four S-oxoacid groups.

The S-oxoacid group includes sulfo group ($-SO_3H$) and hydroxysulfinyl group ($-SO.OH$). The preferred S-oxoacid group is sulfo group.

The term "saccharic carbon atom" refers to a carbon atom which is a member of the tetrahydrofuran or tetrahydropyran ring of the monosaccharide contained in the oligo- or polysaccharide.

The linking group of lower molecular weight includes oxy ($-O-$), imino ($-NH-$), thio ($-S-$), methylene ($-CH_2-$), ethylidene ($-CH(CH_3)-$) groups and the like. The term "lower molecular weight" is intended to mean that the group has a molecular weight from about 14 up to about 32. The preferred linking groups are oxy and imino groups.

One class of the oligo- or polysaccharide is a natural polysaccharide having at least one hydrogen sulfate group ($-O-SO_3H$) and is obtained from a plant or a microorganism, or a synthetic polysaccharide having at least one hydrogen sulfate group ($-O-SO_3H$) and is formed by esterifying a polysaccharide obtained from a plant or a microorganism.

Within this class, a preferable subclass is a polysaccharide composed of non-amino monosaccharide (including sugar acid) as the repeating unit. This polysaccharide, however, may contain a trace amount of nitrogen. Examples of the non-amino sugar repeating units include xylose, arabinose, rhamnose, fucose, glucose, galactose, glucuronic acid, galacturonic acid, mannuronic acid, etc. The natural polysaccharide includes carrageenan (galactan sulfate obtainable from *Gigartina tenella*, etc.) and fucoidin (polyfucose sulfate obtainable from Laminaria brown seaweed). Carrageenan includes κ-carrageenan, λ-carrageenan, ι-carrageenan, etc. which differ in the number of hydrogen sulfate groups present. The synthetic polysaccharide includes those to be obtained by sulfuric acid esterification of polysaccharides, e.g., starch and partial hydrolyzate thereof, dextran which is produced by *Leuconostoc sp.* and partial hydrolyzate thereof (usually having the molecular weight of 500-2,000,000, ordinarily 2,000 and 300,000, preferably 2,000-10,000, most suitably 3,000-8,000, e.g., 7,000-8,000), glycogen, pectin, cellulose, plant viscous liquids (gum arabic, tragacanth gum, etc.), plant mucilage products (those obtainable from *Hibiscus esculentus, Aloe, Brasenia schreberi*, etc.), viscous liquids of marine and fresh water algae (alginic acid, laminarin, etc.) or polysaccharide derived from microorganism (lentinan, pulluran, mannan, exlan, etc.). They include known ones (dextran sulfate, cf., European Patent Laid-open Publication No. 0066379) and novel ones. The dextran sulfate can have a sulphur content of between 5% and 22%, or preferably between 10% and 20%, or most suitably between 15% and 20%. The novel ones may be produced in the same manner as in the known ones. An example of the preparation process is shown, as follows:

Chlorosulfonic acid is added dropwise to dry pyridin of 8-10 fold volume while cooling. To the mixture are added small amounts of formamide and dextran (about ¼ weight of chlorosulfonic acid), and the mixture is heated to 55°-65° C. under stirring. After stirring the mixture for several hours, the solvent is distilled off, and the residue is purified for example by recrystalization, dialysis, etc. The term "polysulfate" is intended to refer to compounds obtained through the sulfuric acid esterification of the polysaccharides of the present invention.

Another class of the oligo- or polysaccharide is a natural polysaccharide having at least one hydrogen sulfate group (—O—SO$_3$H) and is obtained from an animal, or a synthetic polysaccharide having at least one hydrogen sulfate group (—O—SO$_3$H) and is formed by esterifying a polysaccharide obtained from an animal.

Within this class, a preferred subclass is the mucopolysaccharides, which is composed of repeating units of an amino monosaccharide (including N-acyl or NH—SO$_3$H). This compound may further contain as another repeating unit non-amino sugar or an acid derivative thereof. The repeating amino-sugar unit or its N-acylated (preferably N-acetylated) derivatives include glucosamine, galactosamine, N-acetylated derivatives of them, and sulfuric acid ester or partial hydrolyzate of the above compound. Examples of monosaccharide or acid (preferably, hexulonic acid ) includes glucose, galactose, glucuronic acid, iduronic acid, etc. The mucopolysaccharides containing such repeating unit include heparin, keratan sulfate, chondroitin-4-sulfate, chondroitin-6-sulfate, dermatan sulfate, teichuronic acid, hyaluronic acid, heparitin sulfate, chitin, and their partial hydrolyzates, modified derivatives (e.g., partial acylated products), and synthetic polysaccharides containing the repeating unit such as above.

The mucopolysaccharide polysulfates are defined as the products which are synthesized by additional sulfuric acid esterification of the above mucopolysaccharides having sulfate group. This esterification may be carried out, for example, according to the procedure described in Japanese Patent Publication No. 9570/1971. In general, the esterification is carried out by treatment of the mucopolysaccharides with one of sulfating reagents such as concentrated sulfuric acid or chlorosulfonic acid.

These reactions are usually carried out with or without a solvent at low temperature. The reaction product is separated by conventional procedure, e.g., neutralization, concentration, precipitation, recrystallization, chromatography, etc.

The term "pharmaceutically acceptable salt" is intended to mean that the salt has the biological activity of the parent compound and is not unusably toxic at the administration level. Such salt includes the salt of inorganic base such as sodium salt, potassium salt, ammonium salt, etc., and salt of organic base such as diethanolamine salt, cyclohexylamine salt, amino acid salt, etc. These salts are produced from the corresponding acids by the conventional procedures. The above oligo- or polysaccharides and their salts may be used alone or as a mixture with the metal salts such as zinc, aluminum, etc. The oligo- or polysaccharide should be administered at a dose sufficient to produce the effect for the desired treatment. For example, the dosage of the sulfates of the above polysaccharide or their salts sufficient to produce blood concentration for anti-virus activity is generally 0.2–200 mg/kg, preferably 0.5–100 mg/kg. In the case of a human, an amount of about 10 mg–10 g/day, preferably about 50 mg–5 g/day, is administered in 1–4 divisions a day, or as a sustained release form. The administration route can be optional such as oral, rectal, nasal, local(including sublingual), injection(including subcutaneous, intracutaneous, intramuscular and intravenous), inunction etc. The preferred route is selected depending on various factors including kind of active ingredient, condition and age of patient, severity of infection etc.

The dosage of the mucopolysaccharides or their polysulfate or the salts thereof sufficient to produce a concentration for anti-virus activity is generally 0.2–200 mg/kg, preferably 0.5–100 mg/kg. In the case of humana, an amount of about 10 mg–20 g/day, preferably about 50 mg–10 g/day is administered in 1–4 divisions a day, or as sustained release form.

The administration route can be optional such as oral, local, injection, inunction, etc.

For administration, the effective ingredient may be mixed with a pharmaceutical carrier such as organic or inorganic solid or liquid excipient e.g. suitable for internal administration or injection, and administered in the form of the conventional pharmaceutical preparation. Such preparation includes solids (e.g., tablet, granule, powder, capsule, etc.) and liquids (e.g., liquid, emulsion, suspension, etc.), and ointment. The above carriers include starch, lactose, glucose, sucrose, dextrin, cellulose, paraffin, fatty acid glyceride, water, alcohol, gum arabic, etc. If necessary, auxiliary, stabilizer, emulsifier, lubricant, binder, pH regulating agent, isotonicity agent, and other additives in ordinary use may be added.

The toxicity of the above oligo- or polysaccharide is extremely low. For example, the acute toxicity (LD$_{50}$) of sodium dextran sulfate (molecular weight 7,000–8,000, S-content 17–20%) is 21,000 mg/kg when orally, and 4,500 mg/kg when intravenously administered to mice. The acute toxicity (LD$_{50}$) of sodium chondroitin sulfate is 4,000 mg/kg or more when intraperitoneally, and 7,500 mg/kg or more when orally administered to mice. The acute toxicity (LD$_{50}$) of sodium heparin is 1,500–2,000 mg/kg when intravenously injected to mice.

EXAMPLES

The following examples will illustrate the present invention in further detail.

PREPARATION 1

Preparation of chondroitin polysulfate from chondroitin sulfate

Chondroitin sulfate (5 g) was added to 95% sulfuric acid (10 ml) cooled at below −25° C. with stirring. After addition, the reaction mixture was stirred at the same temperature for 90 minutes. After the end of the period, the reaction solution was gradually poured onto ice (120 g) with stirring. To the resulting solution was gradually added calcium carbonate with well stirring. The precipitates were filtered off, which, then were washed well with water. To the combined filtrates (240 ml) was added ethanol (60 ml), and the solution was kept to stand overnight at 5° C. to precipitate calcium sulfate. The precipitates were filtered off, and the filtrate was adjusted to pH 10 with sodium carbonate. After addition of acetic acid to make the solution weakly acidic, the solution was concentrated to about 20 ml, then diluted with ethanol (100 ml), and kept to stand overnight at 5° C. The precipitates in the solution were isolated with centrifugation, washed with ethanol, and with ether, and dried under vacuum to give the white powder of the title compound.

PREPARATION 2

Preparation of keratan polysulfate from keratan sulfate.

Preparation 1 was repeated except that keratan sulfate (100 mg) is used as a starting material and 1 ml in place of 10 ml of 95% sulfuric acid, to give the title compound.

Formulation 1

Sodium dextran sulfate (molecular weight: 7,000-8,000, S-content: 17-20%): 150 mg
Corn starch: 45 mg
Lactose: 300 mg
Magnesium stearate: 5 mg The above ingredients are mixed, granulated, and pressed according to the conventional procedure to make tablets, which were then enterically coated.

Formulation 2

Sodium dextran sulfate (molecular weight: 7,000-8,000, S-content: 17-20%): 600 mg
Physiological saline: q.s. to 10 ml.

Formulation 3

Sodium dextran sulfate (molecular weight: 5,000, S-content: 13-14%): 600 mg
Physiological saline: q.s. to 10 ml.

Formulation 4

Sodium salt of chondroitin sulfate: 150 mg
Corn starch: 45 mg
Lactose: 300 mg
Magnesium stearate: 5 mg The above ingredients are mixed, granulated, and pressed according to conventional procedure to make tablets, which were then enterically coated.

Formulation 5

Sodium salt of keratan polysulfate: 400 mg
Lactose: 195 mg
Magnesium stearate: 5 mg The above ingredients are mixed according to the conventional procedure and filled in hard gelatine capsules.

Formulation 6

Sodium salt of chondroitin polysulfate: 300 mg
Physiological saline: q.s. to 10 ml.

Formulation 7

Sodium heparin: 25,000 units
Physiological saline: q.s. to 10 ml.

Formulation 8

Calcium heparin: 5000 units
Procain hydrochloride: 10 mg
Water: q.s. to 10 ml.

EXAMPLE 1

(Inhibition of reverse transcriptase activity)

Test substances were assayed for inhibition against the enzyme activity of reverse transcriptase (authentic sample) derived from Avian Myeloblastosis Virus (abbrev. AMV), a kind of retrovirus. Five microliters of $(\gamma A)_n$(template RNA), 4 $\mu$l of $(dT)_{12-18}$(primer DNA), and 1 $\mu$l of water were mixed with 5 $\mu$l of 0.5M Tris-CHl (pH 8.4) including 0.1% triton X-100, 5 $\mu$l of 1nM-MgCl$_2$, 5 $\mu$l of 20 mM-DDT, 5 $\mu$l of water, and [$^3$H]-TTP (tritium labeled thymidine triphosphate). To this mixture, test substances in solutions (final concentrations: 1, 0.1, and 0.01 $\mu$g/ml, 5 $\mu$l) or buffer solutions (control, 5 $\mu$l) at various doses were added. Then, 5 $\mu$l (one unit) of the authentic reverse transcriptase derived from AMV was added and the reaction mixture was incubated at 37° C. for 30 minutes. The reaction was stopped by addition of trichloroacetic acid, and after filtering the reaction mixture, the radioactivity of the polymerized ($^3$H-T)n retained on the filter was measured using a liquid scintillation counter. As the test substances, sodium dextran sulfate (molecular weight: 5000), same (molecular weight: 8000), same (molecular weight: 500000), fucoidin, $\kappa$-carrageenan, $\lambda$-carrageenan, and $\iota$-carrageenan were used. The results are shown in FIGS. 1-7.

FIGS. 1-7 show that the enzyme inhibition increases with the increasing doses of the above test substances.

EXAMPLE 2

(Inhibition of reverse transcriptase activity)

The assay procedure of Example 1 was repeated using disrupted HTLV-III virions as a crude reverse transcriptase in order to evaluate the reverse transcriptase inhibitory effect of dextran sulfate (DS, molecular weight 7,000-8,000, S-content 17-20%). The result is shown in FIG. 8.

FIG. 8 shows that DS has an inhibitory effect against the reverse transcriptase derived from AIDS-virus, HTLV-III.

EXAMPLE 3

(Anti-AIDS virus activity)

To MT-4 cells (30×10$^4$/ml) cultured in RPMI-1640 medium containing 10% bovine serum, was inoculated HTLV-III, and the suspension was incubated at 37° C. for 1 hour to cause the adsorption of the virus. The cell:virus ratio was 500:1. The cells were then washed, and cultured with or without various doses of the test substances (same as those of Example 1) at 37° C. under 5% CO$_2$ for 3 days, after which cell growth, viability, and percentage of infected cells were recorded. The infected cells were distinguished from the uninfected cells by indirect immuno-fluorescence method. Thus; the cultured cells were fixed with cold methanol on a slide glass, reacted with antibody to the HTLV-III-specific antigens, and further with the secondary antibody (having fluorescent label). The results are shown in FIGS. 9-29, wherein, ▽, △ and □ show the controls without virus; ▼, ▲ and ■ show the infection experiments with HTLV-III. The cell growth is indicated in number of cells, the viability (%) in number of viable cells×100/number of total cells, and the infected cell rate (%) in number of fluorescent-positive cells×100/number of total cells.

FIGS. 9-22 demonstrate that when no test compound was added to the medium, the cells did not grow and were killed by viral infection, whereas depending on the increase in the dose of the test substance, the number of cells and viability came near to the values of the control without virus. Also, it is shown from FIGS. 23-29 that when the test substance is not added, almost all cells are infected (−100%), whereas depending on the increase in the dose of the test substances, the infection of cells was strongly inhibited.

Accordingly, it is evident that the test substances have excellent inhibiting activities against infection of AIDS virus to host cells and viral proliferation.

EXAMPLE 4

(Cytotoxicity)

As the anti-virus substances often show toxicity to the host cells, the following experiment was conducted to determine whether or not the test substances (used in Example 1 and 3) would induce cytotoxicity.

MT-4 cells were cultured with or without 1-100 µg/ml of each test substance which is the same as in Example 1 and 3 and the proliferation and viability of cells were recorded. The results are shown in the following Table.

| Substance (µg/ml) | Cell number ($\times 10^4$ cells/ml) | Viability (%) |
|---|---|---|
| Sodium dextran sulfate (molecular weight: 5000, S-content: 13%) | | |
| 100 | 121 | 93 |
| 10 | 127 | 92 |
| 1 | 123 | 90 |
| 0 | 124 | 87 |
| Sodium dextran sulfate (molecular weight: 7000-8000, S-content: 17-20%) | | |
| 100 | 130 | 94 |
| 10 | 138 | 91 |
| 1 | 120 | 90 |
| 0 | 124 | 87 |
| Sodium dextran sulfate (molecular weight: 500,000 S-content: 16%) | | |
| 100 | 126 | 86 |
| 10 | 139 | 94 |
| 1 | 124 | 88 |
| 0 | 124 | 87 |
| Fucoidin | | |
| 100 | 71 | 93 |
| 10 | 112 | 99 |
| 1 | 141 | 92 |
| 0 | 124 | 87 |
| κ-Carrageenan 80% + λ-Carrageenan 20% | | |
| 100 | 111 | 92 |
| 10 | 149 | 93 |
| 1 | 147 | 93 |
| 0 | 124 | 87 |
| λ-Carrageenan | | |
| 100 | 83 | 94 |
| 10 | 203 | 94 |
| 1 | 147 | 89 |
| 0 | 124 | 87 |
| ι-Carrageenan | | |
| 100 | 144 | 80 |
| 10 | 128 | 93 |
| 1 | 135 | 94 |
| 0 | 124 | 87 |

The above results show that the test substances have little cytotoxicity.

EXAMPLE 5

(Inhibition of reverse transcriptase activity)

The effects of the test substances on the reverse transcriptase activity of AMV were evaluated by the method described in Example 1. The test substances used are chondroitin sulfate (S-content: 6.2-6.9%), chondroitin polysulfate (S-content: 11.6-12.1%), keratan sulfate (S-content: 7.0-8.0%), and keratan polysulfate (S-content: 9.7%). The results are shown in FIGS. 30-33.

FIGS. 30-33 indicate that the enzyme inhibition increases with the increasing doses of the above test substances. The above results also demonstrate that the reverse transcriptase inhibitory activity of the test substances is closely related to the number of sulfate groups in the molecule, as evidenced by the fact that the synthetic substances (e.g. condroitin polysulfate and keratan polysulfate) have stronger activity than the natural substances (e.g. condroitin sulfate and keratan polysulfate).

EXAMPLE 6

(Anti-AIDS virus activity)

Test substances were assayed for the anti-AIDS virus activity in the same manner as in Example 3 using cell culture. The test substances are the same as those used in Example 5. The results are shown in FIGS. 34–45, wherein ▽, △ and □ show the controls without virus, ▼, ▲ and ■ show the infection tests with virus.

FIGS. 34–41 demonstrate that, without the test substances, the cells did not grow and were killed by viral infection, whereas depending on the increase in the dose of the test substance, the decrease in number of cells and loss of viability were prevented. Also, FIGS. 42–45 demonstate that when the test substance was not present, almost all of the cells were infected ($\simeq 100\%$) with HTLV-III, whereas depending on the increase in the dose of the test substances, the infected cell rate (%) was significantly reduced.

The above results also indicate that the synthetic mucopolysaccharide polysulfates having higher S-content had stronger anti-AIDS virus activities than those of the natural products.

EXAMPLE 7

(Anti-AIDS virus activity)

Figure 48:
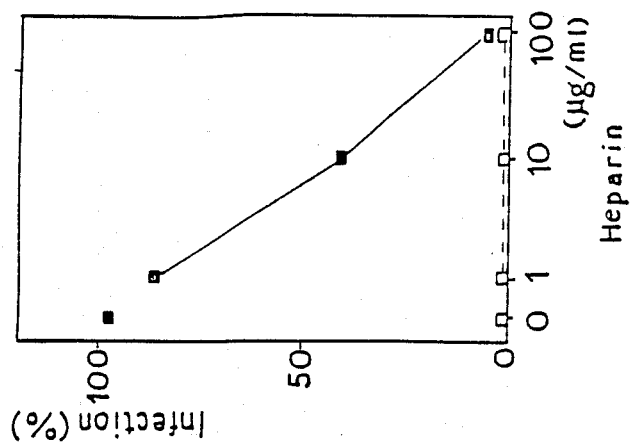
FIGS. 46-48 show the effects of heparin on cell growth, viability and infected cell rate of MT-4 cells infected with HTLV-III, respectively, in Example 7.

The anti-AIDS virus activity of heparin was evaluated in the same manner as in Example 3. The results are shown in FIGS. 46–48, wherein ▽, △ and □ show the controls without virus, and ▼, ▲, and ■ show the infection tests with virus.

Figure 47:
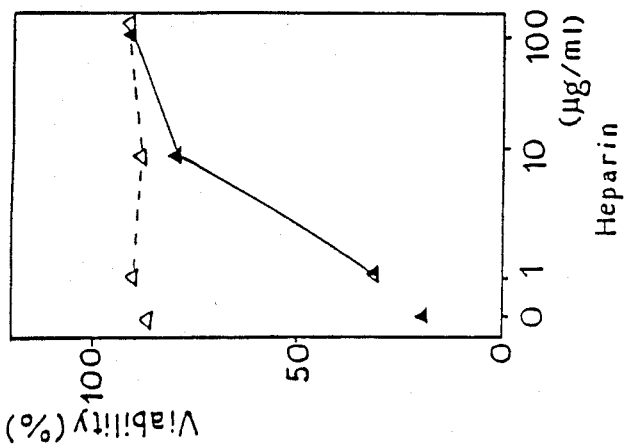
Figure 46:
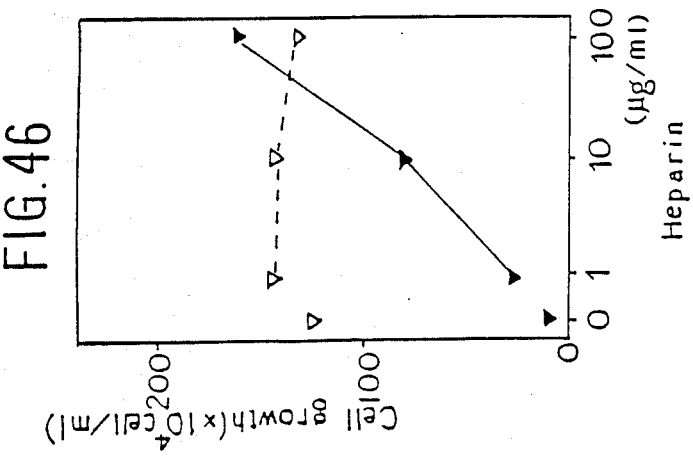

FIGS. 46 and 47 show that without heparin, the cells did not grow and were killed by viral infection, whereas depending on the increase in the dose of heparin, the number of cells and viability were maintained to that of control. It was also shown from FIG. 48 that when heparin was not present, almost all of the cells are infected, whereas depending on the increase in the dose of heparin, they become less susceptible to the viral infection.

EXAMPLE 8

(Cytotoxicity)

As the anti-virus substances often show toxicity to the host cells, an experiment was conducted to know whether or not heparin would induce such cytotoxicity.

Without the virus, MT-4 cells were cultured in the same manner as in Example 4 except the test sample was heparin, and proliferation and viability of cells were recorded. The results are shown in the following Table.

| Heparin (µg/ml) | Cell number ($\times 10^4$ cells/ml) | Viability (%) |
|---|---|---|
| 100 | 133 | 94 |
| 10 | 142 | 89 |
| 1 | 143 | 91 |
| 0 | 124 | 87 |

The above results demonstrate that heparin has little cytotoxicity.

EXAMPLE 9

(Anti-AIDS activity)

In order to examine the correlation between the anti-AIDS virus activity and the molecular structure (especially, molecular weight and S-content or number of sulfate group in this case) of various test substances including those used in Examples 1-7, the anti-AIDS activities were evaluated for the various naturally occurring polysaccharides, polysaccharides having sulfate group, mucopolysaccharides, mucopolysaccharide sulfate, and mucopolysaccharide polysulfate. Further, similar experiments were carried out with various other sulfates which were synthetically obtained. The experimental procedures employed are identical to that in preceding experiments. The cultured MT-4 cells were infected with HTLV-III and the inhibitory effects of various test subsutances on the infected cell rate (number of fluorescent cell × 100/ total cell, %) were determined at 6th day. The results are shown in the following Table.

(number of sulfate group) of the molecule. With respect to the relation with the molecular weight, there was no effect at all in the monosaccharides. However, in the substances having molecular weights of 5,000 and higher, the increase of the molecular weight did not affect the anti-AIDS virus activity as seen in e.g. dextran sulfate.

This is quite different from the pattern of manifestation of heretofore known activities of polysaccharide sulfates against herpes virus.

In view of the fact that the polysaccharides with higher molecular weight and their sulfate are known to have the high toxicities to human being and animals, the experimental evidence obtained in the persent invention that the dextran sulfate with lower molecular weight show sufficient anti-AIDS activity, is extremely important in developing it as a medicament for prevention and therapy of the viral disease.

Among the above test substances, those which showed particularly strong anti-AIDS virus activities are dextran sulfate, λ-carrageenan, alginic acid sulfate,

| Test substance | Molecular weight | S-content (%) | Infected cell (%)* | | |
|---|---|---|---|---|---|
| | | | 10 μg/ml | 100 μg/ml | 1000 μg/ml |
| (1) Dextrans, their synthetic sulfates, and monosaccharides having sulfate groups. | | | | | |
| Dextran | 9,000 | 0 | 100 | 100 | |
| " | 300,000 | 0 | 100 | 100 | |
| Dextran sulfate | 5,000 | ≈13 | 18 | 0 | |
| " | 8,000 | ≈14 | 25 | 0 | |
| " | 500,000 | ≈16 | 20 | 0 | |
| " | 7,000–8,000 | 17–20 | 1 | 0 | |
| " | 3,500 | 6 | 100 | 82 | 1 |
| (Monosaccharides) | | | | | |
| Glucose-6-sulfate | | 12 | 100 | 100 | 100 |
| Glucose-polysulfate | | 22 | 100 | 100 | 100 |
| N—acetylglucosamine polysulfate | | 18 | 100 | 100 | 100 |
| (2) Polysaccharides derived from algae and their sulfates. | | | | | |
| K-Carrageena | | ≈7 | 95 | 1 | |
| γ-Carrageenan | | ≈16 | 3 | 1 | |
| ι-Carrageenan | | ≈12 | 100 | 31 | |
| Fucoidin | | ≈15 | 32 | 1 | |
| Agarose | 60,000–180,000 | 2–3 | 100 | 100 | |
| Alginic acid | 32,000–240,000 | 0 | 100 | 100 | |
| Alginic acid sulfate | 50,000–300,000 | 14 | 7 | 4 | |
| (3) Chitin and chitosan and their sulfates | | | | | |
| Chitin | | 0 | 100 | 100 | |
| Chitin sulfate | | 9 | 100 | 81 | |
| Chitosan | | 0 | 100 | 100 | |
| Chitosan sulfate | | 18 | 1 | 1 | |
| (4) Mucopolysaccharides derived from animals, and their sulfates and polysulfates | | | | | |
| Chondroitin | 25,000–30,000 | 0 | 100 | 100 | |
| Chondroitin polysulfate | 5,000–8,000 | 13 | 3 | 1 | |
| Chondroitin-4-sulfate | 30,000–50,000 | 6 | 90 | 80 | |
| Chondroitin-4-sulfate polysulfate | | 16 | 2 | 1 | |
| Dermatan sulfate | 20,000–40,000 | 6 | 100 | 80 | |
| Chondroitin-6-sulfate | 30,000–50,000 | 6 | 100 | 100 | |
| Chondroitin-6-sulfate polysulfate | | 15 | 2 | 1 | |
| Heprin | 7,000–3,000 | 13 | 41 | 1 | |
| Heparitin sulfate | 15,000 | 7 | 100 | 90 | |
| Keratan sulfate | 4,000–20,000 | 7 | 100 | 60 | |
| Keratan polysulfate | | 10 | 40 | 20 | |
| Hyaluronic acid | 10,000–100,000 | 0 | 100 | 100 | |
| Hyaluronic acid sulfate | | 8 | 100 | 70 | |

*The control without test substance shows the value of 100% as the infected cell rate under the same conditions.

(5) Other polysaccharides pectin, colominic acid, inulin, raffinose, neither methylcellulose showed any anti-AIDS virus activities.

From the above results, it can be clearly seen that the anti-AIDS virus activity is closely related to the S-content or number of sulfate groups in this case rather than to the molecular weight. Substances lacking sulfate group showed no anti-AIDS activity. Further, the anti-AIDS activity was intensified with increasing S-content chitosan sulfate, chondroitin polysulfates, further sulfated chondroitin-4-sulfate and -6-sulfate, heparin, etc. having S-content more than 10%.

EXAMPLE 10

(Anti-Friend leukemia virus (F-MuLV) activity)

(Procedure 1)

Anti-FMuLV activity of dextram sulfate (molecular weight: 7000-8000, S-content: 17-20%) was determined by a XC-plaque assay method. BALB3T3 cells were cultured in adhesive form in a 35 mm-dish at $5 \times 10^4$ cells/dish (2 ml). After removing the culture medium, a fresh medium with or without indicating concentrations of the test substance (1 ml each) and 0.2 ml of the virus preparation were charged, and the cells were cultured overnight. On the following day, the culture media were replaced with those (2 ml) containing or not containing the above substances, the incubation was continued for three additional days to progress the infection and replication of the virus. After the removal of the medium, the further progression of viral replication was stopped by UV irradiation. To this dish, the suspension of XC-cells (2 ml) was added and cultured for three days and the plaque formation produced by the virus particle induced cell-fusion, was observed. The number of plaques was shown in the following Table.

TABLE

| Anti-Freind leukemia virus activity by Procedure 1 | | |
|---|---|---|
| DS (μg/ml) | Number of plaques per dish | Inhibition (%) |
| Control | 168 | (0) |
| 1 | 14 | 92 |
| 5 | 12 | 93 |
| 10 | 11 | 93 |
| 50 | 13 | 92 |
| 100 | 6 | 96 |
| 1000 | 0 | 100 |

As observed from the above Table, DS inhibited 90% or more the formation of plaque at the concentrations of 1-100 μg/ml, indicating that the infection and replication of the virus was strongly inhibited. The plaque formation was not detected at 100 μg/ml of DS.

DS at 1-100 μg/ml did not show any cytotoxicity to BALB 3T3 cells.

(Procedure 2)

Procedure 1 was repeated except that after adsorption of the virus in the medium without DS, the non-adsorbed viruses were removed and the culture was carried out in the medium (2 ml) containing or not containing DS. The results are shown in the following table.

TABLE

| Anti-Friend leukemia virus activity by Procedure 2: | | |
|---|---|---|
| DS (μg/ml) | Number of plaques per dish | Inhibition (%) |
| Control | 35 | (0) |
| 0.01 | 33 | 6 |
| 0.1 | 19 | 45 |
| 1 | 14 | 61 |
| 10 | 17 | 52 |
| 100 | 16 | 54 |
| 500 | 0 | 100 |

The above results indicate that, also in Procedure 2, DS inhibited the infection and replication of the virus by about 60% at the concentration of 1 μg/ml, and almost completely at 500 μg/ml.

From the above results, it is evidenced that DS inhibits the infection and replication of the oncogenic virus (Oncovirinae) including F-MuLV, as well as the cytolytic virus (Lentivirinae) including AIDS-virus.

What is claimed is:

1. A method for inhibiting infection of human T-cells by a human retrovirus which comprises providing in the presence of human T-cells susceptible to infection by said human retrovirus an infection inhibiting effective amount of dextran sulfate having a sulfur content of between 13 and 20%.

2. The method of claim 1 wherein said human retrovirus is a human immunodeficiency virus.

3. The method according to claim 1, wherein said human retrovirus is selected from the group consisting of human T-cell lymphotropic virus-III, lymphoadenopathy associated virus, and AIDS-related virus.

4. The method according to claim 1, wherein said human retrovirus is selected from the group consisting of human T-cell lymphotropic virus-I, human T-cell lymphotropic virus-II, and Kawasaki disease causative retroviruses.

5. The method of claim 1 wherein said dextran sulfate has a sulfur content of between 17 and 20%.

6. The method according to claim 1 or claim 5 wherein said dextran sulfate has a molecular weight between 500 and 2,000,000.

7. The method according to claim 6 wherein said dextran sulfate has a molecular weight between 2,000 and 300,000.

8. The method according to claim 6 wherein said dextran sulfate has a molecular weight between 2,000 and 10,000.

9. The method according to claim 6 wherein said dextran sulfate has a molecular weight between 2,000 and 8,000.

10. The method according to claim 6 wherein the dextran sulfate has a molecular weight between 2,000 and 6,000.

11. The method according to claim 6 wherein the dextran sulfate has a molecular weight between 7,000 to 8,000.

* * * * *